US011135081B2

(12) United States Patent
Johnson et al.

(10) Patent No.: US 11,135,081 B2
(45) Date of Patent: Oct. 5, 2021

(54) METHOD FOR AUTOMATING CUSTOM-FITTING JOINT BRACE

(71) Applicant: Icarus Medical, LLC, Charlottesville, VA (US)

(72) Inventors: David T. Johnson, Charlottesville, VA (US); Xue Feng, Silver Spring, MD (US); Evan Eckersley, Charlottesville, VA (US); Benjamin Scire, Hopkinton, MA (US); Charles Rushton, Dallas, TX (US)

(73) Assignee: Icarus Medical, LLC, Charlottesville, VA (US)

( * ) Notice: Subject to any disclaimer, the term of this patent is extended or adjusted under 35 U.S.C. 154(b) by 0 days.

(21) Appl. No.: 17/211,590

(22) Filed: Mar. 24, 2021

(65) Prior Publication Data

US 2021/0205110 A1    Jul. 8, 2021

Related U.S. Application Data

(60) Continuation-in-part of application No. 17/074,542, filed on Oct. 19, 2020, which is a division of
(Continued)

(51) Int. Cl.
*A61F 5/01* (2006.01)
(52) U.S. Cl.
CPC .... *A61F 5/0125* (2013.01); *A61F 2005/0139* (2013.01); *A61F 2005/0165* (2013.01)

(58) Field of Classification Search
CPC ............ A61F 5/0125; A61F 2005/0139; A61F 2005/0165; A61F 13/048; A61F 13/107;
(Continued)

(56) References Cited

U.S. PATENT DOCUMENTS 8,538,570 B2    9/2013   Stanhope et al.
8,838,263 B2    9/2014   Sivak et al.
(Continued)

FOREIGN PATENT DOCUMENTS

AU    2012289973 B2    1/2017
CN       102209965 B    6/2014
(Continued)

*Primary Examiner* — Tarla R Patel
(74) *Attorney, Agent, or Firm* — Woods Rogers PLC; Nathan A. Evans

(57) ABSTRACT

An automated method for applying specific geometric constraints to a starter file and considering external specifications outside of fit to achieve an optimized, restorative joint brace or orthotic device. External specifications may include indications of the patient, biometric data, data from prescribing doctors, X-ray data, MRI data, joint geometry to restore optimized function, and envelope of motion. After the fitting process, the starter file undergoes a process of exact commands in order to finish and/or add additional features. With a vertical integration from scanning an object to producing the custom fitted device, the product can be manufactured at scale more rapidly and at lower cost, improving access to superior devices at a reasonable price to the consumer.

23 Claims, 3 Drawing Sheets

Related U.S. Application Data application No. 15/585,968, filed on May 3, 2017, now Pat. No. 10,806,619, application No. 17/211,590, which is a continuation-in-part of application No. 17/074,571, filed on Oct. 19, 2020, which is a continuation-in-part of application No. 15/585,968.

(60) Provisional application No. 62/331,315, filed on May 3, 2016.

(58) Field of Classification Search
CPC .. A61F 2013/49096; A61F 5/01; A61F 5/026; A61F 5/028; A61F 2/30; A61F 2002/30624
See application file for complete search history.

(56) References Cited

U.S. PATENT DOCUMENTS

| | | |
|---|---|---|
| 9,201,988 B2 | 12/2015 | Stanhope et al. |
| 9,610,731 B2 | 4/2017 | Zachariasen |
| 10,482,187 B2 | 11/2019 | Summit et al. |
| 10,806,605 B2 | 10/2020 | Herr et al. |
| 2002/0059049 A1 | 5/2002 | Bradbury et al. |
| 2009/0313853 A1* | 12/2009 | Tadin ........................ B32B 5/26 36/91 |
| 2011/0009787 A1* | 1/2011 | Pallari ................... A61F 5/0127 602/16 |

FOREIGN PATENT DOCUMENTS

| | | | |
|---|---|---|---|
| EP | 2671544 A2 * | 12/2013 | ........... A61N 1/0452 |
| JP | 5969440 B2 | 8/2016 | |
| WO | 2010120990 A1 | 10/2010 | |

\* cited by examiner

METHOD FOR AUTOMATING CUSTOM-FITTING JOINT BRACE

CROSS-REFERENCE TO RELATED APPLICATIONS

The present application is a continuation-in-part of and relies on the disclosures of and claims priority to and the benefit of the filing dates of U.S. patent application Ser. Nos. 17/074,571 and 17/074,542, filed Oct. 19, 2020, which rely on the disclosures of and claim priority to and the benefit of the filing date of U.S. patent application Ser. No. 15/585,968, filed May 3, 2017, which claims priority to and benefit from U.S. Provisional Patent Application No. 62/331,315 filed on May 3, 2016. This application also relates to and relies on the disclosures of and claims priority to and the benefit of the filing date of PCT/US2020/047904, filed Aug. 26, 2020. The disclosures of those applications are hereby incorporated by reference herein in their entirety.

The disclosures of those applications are hereby incorporated by reference herein in its entirety.

BACKGROUND OF THE INVENTION

Field of the Invention

The current invention provides a method for computer aided design and manufacturing of a custom-fitted joint brace, such as a knee brace, and included braces made by conventional techniques, three-dimensional ("3D" or "3-D") printing, additive manufacturing, thermoformed, pultrusion, extrusion, and other methods of making a knee brace component. More specifically, the invention provides for automated design and manufacture of orthotic and prosthetic devices.

Because of the required uniqueness of each device depending on the user, custom form-fitting medical technology requires significant time to measure, design, and manufacture an appropriate product. This invention shortens the time required to create custom medical technology for the alleviation of pain, structural support, or realignment of joints/bones/limbs. It also increases the precision of the fit to improve comfort and wear-ability while reducing sliding, addressing major limitations of other braces that reduce user compliance, adoption, and overall efficacy. Through capture and processing of data including 3D data, patient data, radiographic data, and biometric data, the invention can achieve a higher degree of customization with the aim of joint restoration, pain relief, or fulfilling other unique user needs. This automated design could not be generated with the current state of the art based on a 3D scan, which alone represents the current state of a joint. It requires further incorporation of data on internal joint geometry and condition (the degree of osteoarthritis ("OA"), cartilage degeneration, or bone, tendon, ligament or muscle deformity) as described herein, prescribed data from a doctor or other medical practitioner (e.g. a need for varus or valgus correction to alleviate pain) in a manual or automated process based on qualitative and quantitative data. Additionally, fit may be improved (for comfort and performance/prevention of sliding/optimizing axis of rotation) based on data such as age, gender, BMI, body weight, height or user activity and lifestyle to increase the brace's lever arm for torque generation and PF compartment unloading, improve fit based on degree of adipose tissue present and need of compression for adherence to the thigh, and optimize axis of rotation based on data that represents the envelope of motion of a joint, which may be collected based on a series of scans or images, a video, or a 3D video capture, as described herein.

Description of Related Art

Within the relevant industry, custom fit medical devices currently are able to form fit the patient using a three dimensional digital representation of the human body or a negative of said body part. After traditional postprocessing, individuals perform finite element analysis (FEA) on the form fit medical devices to determine if the device satisfies the design restraints. However, the current process exists only for individual customers and cannot be successfully scaled to large groups—allowing for a reduction of cost and time, a more available product, and more consistent, high quality products. Additionally, the design of devices based on these methods are based on 3D scan data, which only captures the external surface of the leg. It does not account, for example, for deformities and generate devices that provide corrective forces to achieve an optimized joint state.

Further, the current state of technology lacks an autonomous process for generating a computer-aided design (CAD) for a custom-fit medical device. Additionally, the medical devices currently produced are narrowly tailored—focused heavily on form-fitting and space constraints. Accordingly, there exists a technological need for an autonomous process taking into account multiple dimensions—including but not limited to strength, comfort, pain relief, form fitting, patient features including joint geometry, degree of OA in each joint, amount of adipose tissue (e.g., extrapolated by BMI), that is truly custom to the patient's shape as well as their indications, envelope of motion, axis of rotation, and gait pattern.

Related references that are not necessarily prior art include U.S. Ser. No. 10/806,605B2, U.S. Ser. No. 10/482,187B2, U.S. Pat. No. 9,610,731B2, U.S. Pat. No. 9,201,988B2, U.S. Pat. No. 8,838,263B2, CN102209965B, JP5969440B2, U.S. Pat. No. 8,538,570B2, AU2012289973B2, WO2010120990A1, and US20020059049A1.

SUMMARY OF INVENTION

The current invention is embodied by a holistic process comprising the capturing of a three dimensional mesh, processing the data, using the cleaned data to perform restricted movements on a base feature, materializing an individual device, checking the quality/of that device, and sending to manufacture through software integration.

In stage one of the process, in an aspect, data representing the 3D digital object of one or more parts of the body is captured. For the purpose of this disclosure, in aspects, a 3D digital object captures the following: a series of points generated by a 3D scan and a negative of a body part representing the surface morphology. The object may be generated by a digital scan using an application ("app") on a cell phone, table computer, computer, digital camera, or other digital device, and a compilation of two-dimensional data sets (e.g., photos taken from different angles). The 3D digital object represents a surface to which a device may be relatively fit or contoured. The 3D digital object may be generated indirectly, for example by making a cast of the body part and then scanning the cast.

3D digital objects may be captured through a range of motion capture to record or measure the envelope of motion of a joint (e.g., the knee from full flexion through full extension).

Additional data may be collected and input to the system manually or automatically. Such data may include, for example, quantitative data from a prescribing doctor including Q angle of the knee, patient biometric and user data such as BMI, and qualitative data such as degree of patient pain, location of pain, and pain during movement. Further data may be indirectly generated with pre-defined functional relationships to initial data inputs. For example, the degree of elasticity or mechanical impedance of the thigh, calf or other body part may be interpolated from age or BMI based on previously defined functional relationships. Another example is the determination of required ultimate strength, yield strength, mechanical advantage, or other specifications of a device based on the user's daily work or activity.

Radiographic data may be included to instruct on device shape for corrective purposes, to restore healthy joint geometry, or to unload a region of the joint.

Data, which is cleaned, compiled and processed through the code, maps specifications for modifications to a base file for the brace or brace part, for example a knee brace product line. This base file can be generated from the imported data or an external file being called up within the code. A base file is made up of one or more objects and sub-objects. "Objects" is a variable, data structure, or any other form of data within the digital design software. Once the base file is in use, an algorithm, which may consist of one or more parameters, moves specific objects into a proper location using translation and/or rotation based on the prior mentioned specifications. Each object can be limited to move in one to three axes of motion and be restricted to rotation to zero or all three axes. Additionally, the object can choose to elect specific points to be referenced by these movements. By placing restrictions on the degrees of freedom of objects, the algorithm can take into account factors outside of simply a direct fit to the data.

A base file may initially comprise one or more parts, which are further divided into component parts before, during, or after modification. For example, a base file for a knee brace may be divided into a top frame and a bottom frame.

After the base device or component is structured into a custom part, additional components or features can be added. Referencing either the imported data, other objects, and/or the base frame or components, a series of scripts are executed to create additional features. These features include but are not limited to strapping systems, tensioning systems, gear systems, additional support, ergonomic design, serialization, logos, or custom aesthetics to yield a final device. Such features may undergo digital transformations, including but not limited to scaling, translation, rotation, textural modification, and infill pattern or density modification.

Following digital generation of the final device, the software may optionally run a script for at least one quality control verification. The check may verify features important for mechanical strength, fit, and orientation. For example, cross sectional area and orientation of strap slots on a brace may be verified relative to one or more objects or data points from the original 3D digital object or other objects in the device itself.

The software may be fully integrated with a fabrication system (e.g., 3D printing database) to automatically enter a fabrication queue for manufacturing. The entire process from scan to print and even through assembly and packaging may be fully or partially automated based on specific application programming interfaces from the scanning or data input on one or multiple devices, to data processing, to automated digital modeling and quality control, to fabrication at a local or remote manufacturing location and may, in aspects, be completed within 12 hours.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

A reference object is defined as one or more points, lines, curves, splines, axes, shapes, planes, cross-section, other two-dimensional objects, meshes, wireframes, other three-dimensional objects, and/or a combination of the preceding list.

DETAILED DESCRIPTION OF THE INVENTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

The invention provides for a manufacturing method starting, in aspects, from a biological body study until fabrication. An example workflow is followed; however, the stages may be reordered, skipped, or modified depending on the application.

While knee braces and orthotics are used by example to describe embodiments of the invention, one skilled in the art would understand that the following descriptions could be applied to any orthotic, prosthetic, wearable device, or user interface (e.g., a handle, vehicle seat, controller, etc). Further, the current invention as described herein could not only be applied to knee braces or orthotics, but could also be used for neck, shoulder, hip, wrist, handle, ankle, and foot applications, by way of example only. Furthermore, the current invention could be applied to wearable technologies and accessories including custom performance wear, watches, helmets, military gear, and footwear by way of example only.

Figure 1:
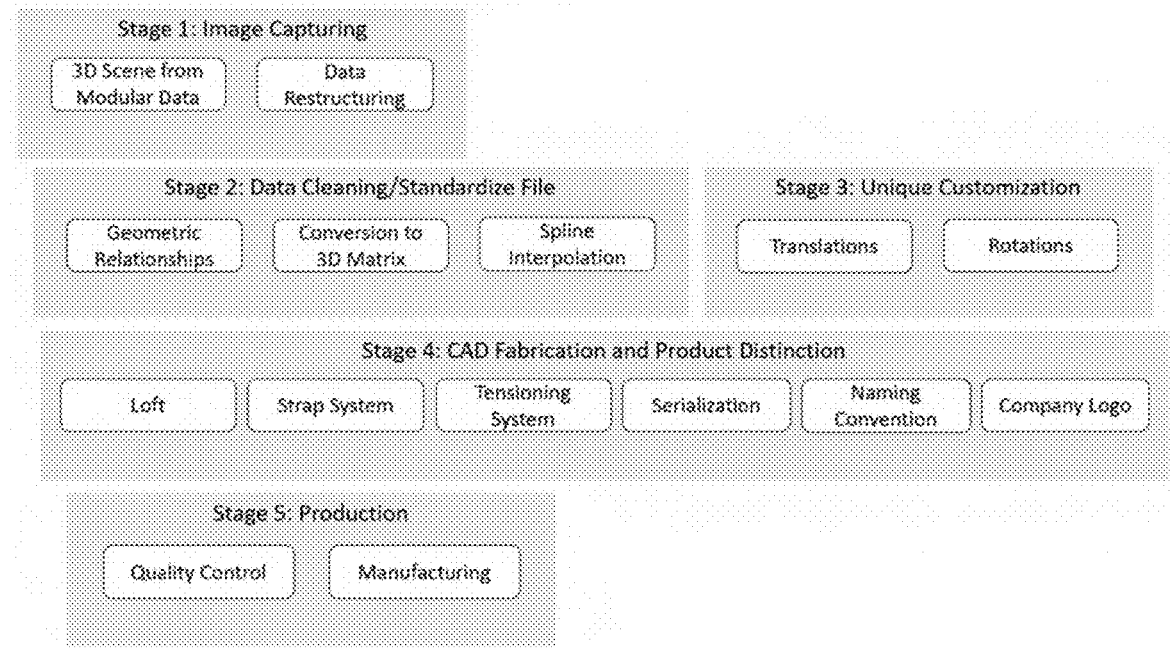
FIG. 1 depicts an exemplary form of a fully or partially automated process, with vertical integration of generating a medical device from data collection (e.g., scan) to fabrication.
Figure 2:
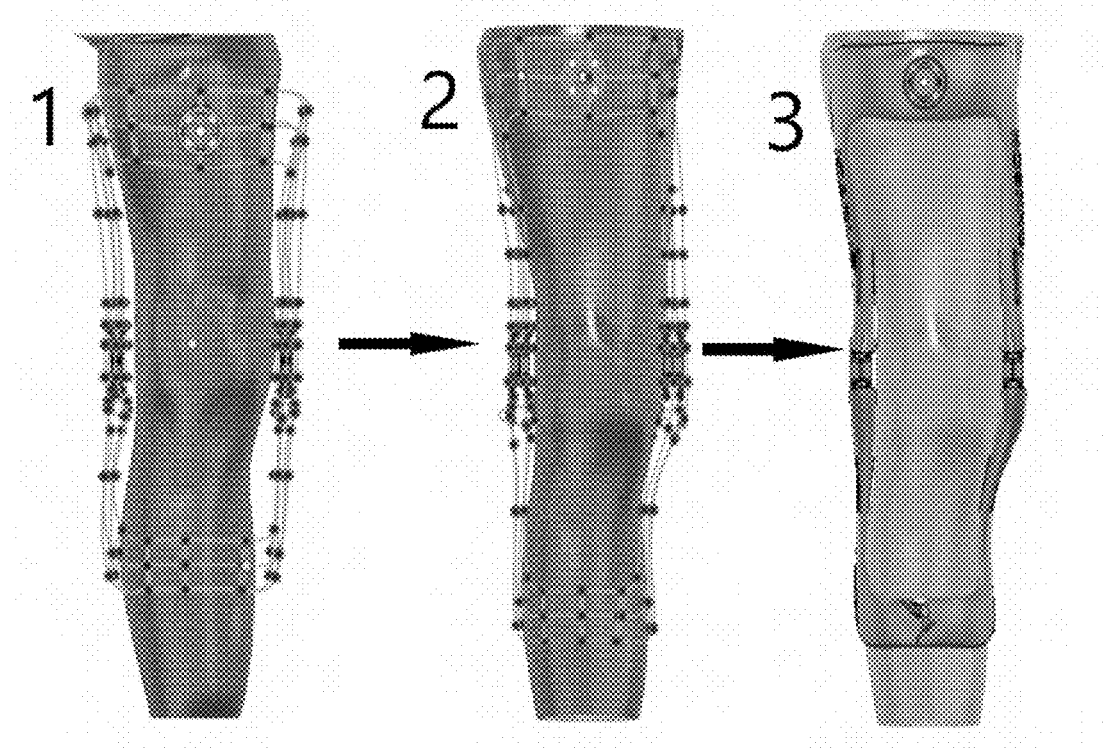
FIG. 2 depicts an automated process according to the invention described herein with a rendered base file for a custom knee brace (1), its transformation to fit to a 3D digital object based on geometric constraints (2), and completed generation of a custom knee brace following addition of components and features, and quality control (3).
Figure 3:
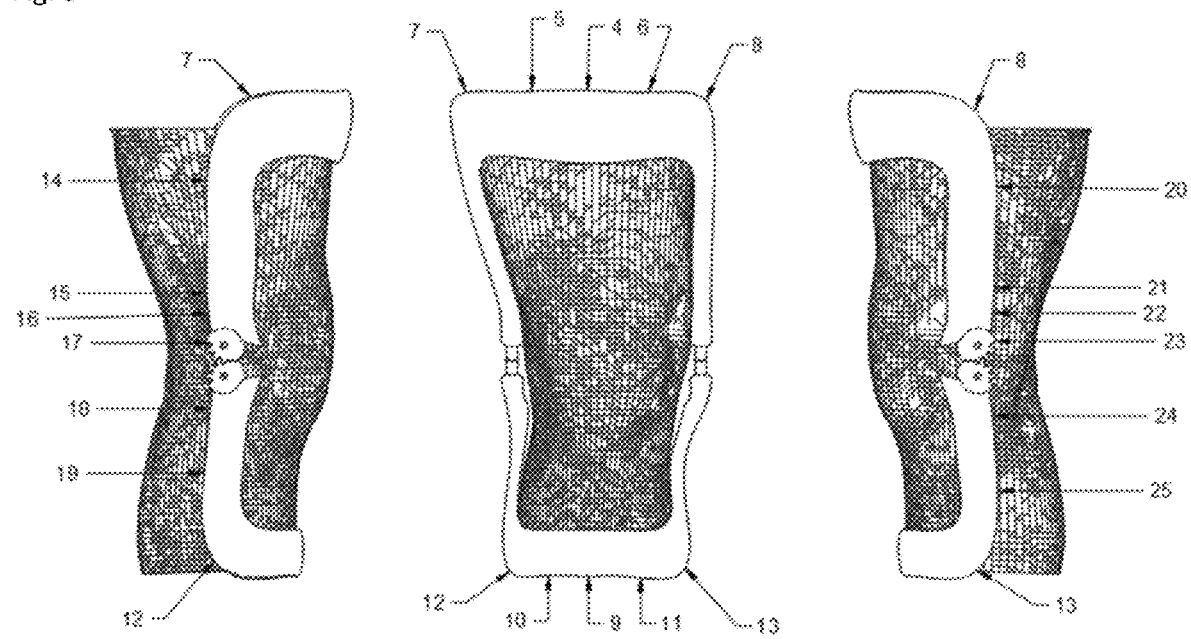
FIG. 3 depicts an example of what a computer aided design file could perform in stage 3 of FIG. 1. Numbered elements 4-25 point to a reference object. A combination of these bodies creates one or more medical devices.
Figure 4:
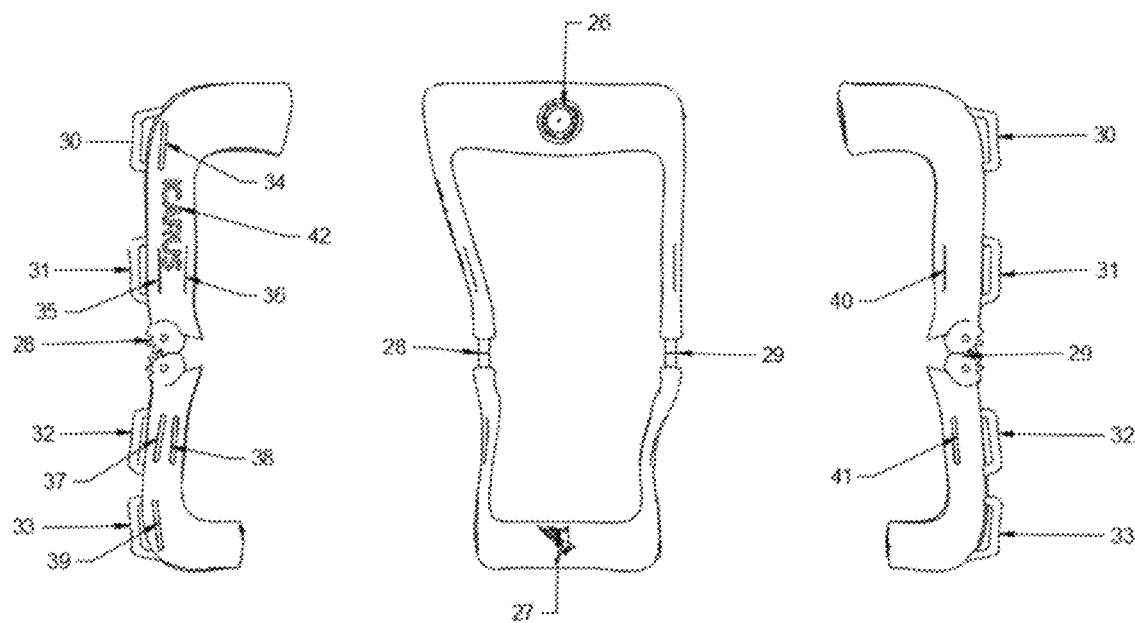
FIG. 4 depicts an example of what a computer aided design file could perform in stage 4 of FIG. 1. Element number 26 indicates a tensioning sub-system. Element number 27 indicates an engraving of the company logo. Element numbers 28-29 indicate a rotation system. Element numbers 30-33 indicate a strapping sub-system. Element numbers 34-41 indicate an additional strapping sub-system. Element number 42 indicates an engraving of the company name.
Figure 5:
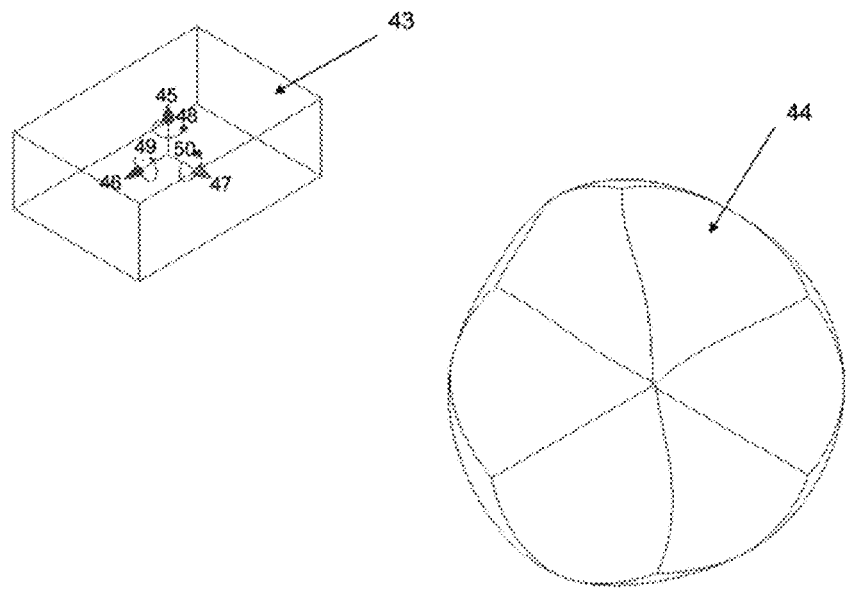
FIG. 5 depicts the high-level representation of stage 3 of FIG. 1. Element number 43 indicates a reference object. Element number 44 indicates input data. Element numbers 45-47 represent the axis coordinate system. Element numbers 48-50 represent the rotational freedom of a reference object. Depending on the reference object, the degrees of freedom may be limited—meaning that the reference object may not be able to follow the direction numbers 45-50.

An exemplary embodiment of the process outlined below is represented in FIG. 1.

Stage 1:

For a desired part or parts of the body for which the device, wearable or user interface is being designed, data is collected, which is then processed to render a 3D digital object. In embodiments, this object may be generated using a 3D scan on a device such as a phone, depth camera, tablet computer, or other computer device. The 3D digital object represents a surface to which a device may be relatively fit or contoured. The 3D digital object may be generated indirectly, for example making a cast of the body part and then scanning the cast. The 3D digital object may be generated based on data representing at least 4 points in space (any number of data points that could represent a 3D object or space) or measurements. For example, circumference measurements of the thigh and calf taken manually by a physician may be input into a system, which will render a 3D leg based on a formula of prior measurement data in combination with or independently from 3D scan data or 2D pictures.

In aspects, internal body components (e.g., bones, tendons, cartilage) may be digitally rendered or captured using the 3D scan alone or in addition to other technologies, such as ultrasound, magnetic resonance imaging, x-ray, or scan. In aspects, internal body components may be digitally rendered as a function of the 3D scan data, measurements, or in reference to the 3D digital object.

3D digital objects may be captured through a range of motion to capture the envelope of motion of a joint (e.g., the knee from full flexion through full extension or an ankle in multiple axes of rotation).

Additional data may be collected and input into the system manually or automatically. Such data may include quantitative data from a prescribing doctor including Q angle of the knee, required varus or valgus correction, required range of motion limitation or augmentation, required support or assistance (e.g. unloading that may be provided by a device that generates force in one or multiple directions). Such data may include patient biometric data or user data such as BMI, age, gender, height, weight, current activity level, desired activity level, and mechanical impedance or elasticity of a part of the body. Such data may include patient qualitative data such as degree of patient pain, location of pain, pain during movement or different activities, pain throughout a range of motion, and desired device use, user activity, or lifestyle.

Further data may be indirectly generated based on initial data inputs. For example, the degree of elasticity/mechanical impedance of the thigh, calf or other body part may be extrapolated from BMI and/or age based on previously defined functions. This would allow for automated design of a device that has dimensions or mechanical properties to provide more compression or a tighter fit in the thigh region, allowing for a better fit, less sliding, and improved performance.

Radiographic data may be included to instruct on device shape for corrective purposes to restore healthy joint geometry or unload a region of the joint. In embodiments, data collection may include individually or combinations of Magnetic Resonance Imaging (MRI), Computed Tomography (CT) scan, Position Emission Tomography (PET) scan, X-ray, fluoroscopy or ultrasound data. Such data may reveal cartilage degeneration or osteoarthritis in a joint, inflammation, deformity or damage of bone, cartilage, muscle, tendon, ligament, nerves, skin/epithelium or other tissue, that would automatically or semi-automatically inform device design to correct joint geometry, prevent undesired or unnatural motion, enhance desired motion, or bias the movement of a joint to reduce user pain, for example during gait or a specific activity.

Objects may be represented as a mesh or other digital file format, a matrix of points, a series of splines or a stack of 2D geometries among other representations to form a 3D digital object.

The data is either transferred to a larger database (e.g., external hard drive, server, or the cloud) or used/stored on the capturing device. During the transferring of files, the data may or may not be converted into a new file format. The file may be converted to or from the following formats, however, this list is non-exhaustive: ply, stl, obj, and usdz file extensions. For example, a 3D scan collected on a smartphone app may be stored in a cloud database as a usdz file, which may be further converted to an obj file that becomes the reference object for design in Stage 2.

Stage 2:

The following stages may be done in any particular order. An example is illustrated below. The data file from stage 1 may be cleaned to remove irregularities, soften extrema, connect surfaces, or modify locations. Cleansing may take the form of removing, adding or joining points, lines, planes, or surfaces. Data compression may also occur to improve overall efficiency, reduce operation time, and minimize required computing power.

In embodiments, within a computer-aided design ("CAD") file, one or more reference objects have specific geometric constraints. An example of a file would include a multitude of cross sections serving as a fluid wireframe of the device. Additional lines, acting as rails, would run through a specific point within each cross section to define the bounds of the device. These geometries can serve as a standard baseline for the shape of the device, allowing for automatic adjustment of this file given the inputs from stage 1. Additionally, 3D objects may also exist within the standardized file if those objects will be added to the final customized device. An example would be using a barrel bolt to connect separate parts of the device. Another example would be using the same sub-component in any version of said device such as a gear that is present regardless of the input data. These reference objects can be preset, generated, or modified based on the input data from stage 1. An algorithm may set the geometric constraints of each object based on the input provided and direct or indirect reference to other objects, data points, surfaces, or splines within the file. For example, a cross-section of the device may be grounded (e.g., unable to move or rotate in any coordinate direction) for a specific design constraint regardless of the position of the mesh. The algorithm's specific transformations, including rotation, translation, mirroring and isotropic or anisotropic scaling for fitment, will be overruled by the geometric constraint and that specific object will remain unmoved. In aspects, the geometric constraints limit the translation by modifying vector components in the $e_i$, $e_j$, $e_k$ directions—where "e" represents an orthogonal axis in some coordinate system. Additionally, the geometric constraints may limit rotation around any axis by modifying components within a three-dimensional matrix transformation or other data format which stores and/or modifies the orientation of an object.

Stage 3:

Once a reference object (43) possesses geometric constraints, transformations including translations (45-47), rotations (48-50), mirroring, and/or isotropic or anisotropic scaling are performed to move a reference object into a new location. These movements may be determined by the data illustrated in Stage 1. Transformations may also be applied to reference objects as a whole or in part to optimize fitment. After one or more reference objects are in the correct location, the algorithm described in Stage 2 may be reapplied with the new location of the reference objects as an input. As such, the objects will be translated, rotated, transformed or scaled relative to the geometric constraints as defined by the data of Stage 1. For example, the geometry and fit of a top brace frame (4-8) may be defined by multiple objects that are further defined by the geometric constraints. An object defining the position of a rotary element (17, 23) may be positioned relative to the top frame and combined with or separated from one or multiple parts of the device based on these constraints and the characteristics of the base device.

In embodiments, the base device may be divided into two or more component parts prior to, during, or following modifications. The components may then undergo further modifications and transformations. For example, a knee brace base device may be divided into a top frame and a bottom frame, with an articulating hinge interface. As another example, a base device for an ankle orthosis may be transformed as one complete unit to fit the user's ankle, heel and foot. The file may then be divided into a custom fit ankle cuff and a custom fit foot orthotic, which may be attached by other components during assembly.

In other embodiments, qualitative and quantitative data from physicians or patient surveys input in Stage 1 may lead to modifications of the device. For example, an individual indicative pain on the medial side of the knee with a recommended Q angle correction of 3° would adjust the brace frame for a correction to unload the medial compartment of the knee using the positioning of objects such as specific cross sections of the frame or gears.

In other embodiments, radiographic information may lead to automated adjustment of the device. For example, the identification of arthritis in the medial compartment of the knee may trigger a similar brace frame adjustment as described in the previous example.

In other embodiments, patient data, including biometric data, may lead to automated adjustment of the device. For example, for an individual with an above average BMI, the top brace frame may be adjusted for a tighter fit and greater compression of the adipose tissue in the thigh.

In other embodiments, scan data showing envelope of motion for a joint may adjust design to optimize the axis of rotation of a device throughout a range of motion. The adjustment may limit or augment movement of the joint or body point in a given direction based on a gait pattern in combination with or independently from data from the physician or radiographic data. For example, the length of a slot in a hinge through which a bolt travels during brace flexion and extension may be limited to reduce the travel of the bolt, thereby limiting the user to a range of motion of 20° to 125° of flexion.

Stage 4:

Whether directly modifying the CAD software or through an application programming interface (API), a series of one or more three-dimensional modeling techniques can be applied to a base device to create the manufacturable device. One or more geometries or features may be generated and added to the fitted model at this stage. Additionally, both additive and subtractive techniques may be applied to add in individual components or subsystems to the device. These subsystems may include a strap system (30-33 and 34-41), tensioning system (26), and resistance system or any system necessary for the application of the device. In embodiments, the types of bodies generated automatically or semiautomatically may be based on the type of device or corresponding base device of the program. For example, a product identified as knee brace type 2 model 3 could generate 4 D-rings (30-33), 8 strap slots (34-41), a boa insert on the upper frame (26) and a mechanical gear interface (28-29). The shape, dimensions, positioning, orientation and design of the component may be defined based on the base device. In embodiments, the characteristics of the component will be defined directly or indirectly as a function of the data collected in Stage 1, including 3D scan data, patient data, radiographic data, and intended use data. The component may be further characterized directly or indirectly as a function of the geometric constraints and objects defined in Stage 2. In other embodiments, the characteristics of the components will be defined relative to or as a function of the dimensions, positioning, or curvature of all or part of the modified base device generated in Stage 3. The components may be modified in groups (each component within the group experiencing the same modification), subgroups, or as individual components. One type of modification, for example scaling and dimensions, may be applied uniformly and simultaneously to a group before individual components within that group go through a separate type of modification (e.g. rotation), which may provide improvements in the efficiency or accuracy of the program. In embodiments, the components may be generated or modified in stages and characteristics defined as a function of other components previously generated.

The modified base file and components may be further modified to alter the shape, surface curvature, texture, printing pattern, or infill pattern. The modifications may be applied in part or in whole. The modifications may impart beneficial mechanical properties at regions of the device. For example, a cross sectional geometry may be applied in a region of the device that will experience a higher degree of compression in one or multiple directions to provide greater durability under load. This may also optimize the device's overall strength to weight ratio. The infill density or infill pattern may be automatically adjusted in regions of the device for similar purposes. The infill pattern, density, or other modifications may be performed only on select components or on the combined base device and components (the whole device) in a predefined gradient. It may be defined or applied based on geometric properties or constraints, such as thickness of the part at a given cross section, relative position from a point, spline, object or other geometric feature. In embodiments, it may be defined/applied based on analysis of the strength or flexibility of the object, which may be determined dynamically or at a specific stage of the process with mechanical analysis such as finite element analysis.

Parts of the base device, components, or the interface between components and the base device or between components themselves may be further modified with techniques including but are not limited to extrusion, combining, lofting, sculpting, and rotations. Techniques (e.g., fillets, chamfers, and holes) may be applied to the digital representation of the manufacturable device to convert the base device into a usable product. Modifications from such techniques may further improve the fit of a device to a body part or improve the strength of the device overall. For example, fillets may be added at the interface of components, such as D-rings or strap slots, with the base device to eliminate stress concentrations. Filets may be applied throughout the device in one or multiple automated stages that eliminate sharp angles or interfaces to eliminate stress concentrations, improve strength at critical failure points, and improve the device's strength overall. Filets or surface smoothing may also be applied to areas of the device that will contact the skin, which may be determined by the proximity of parts of the device to the 3D digital object (e.g., leg scan). This can eliminate sharp edges to maximize comfort for the user.

After the device's main form is created, product distinction techniques may be applied. This may include serial numbers, custom names, custom engravings, company logo engravings, and company name engravings. Such distinction features may be automatically generated based on the initial data input, the geometric constraints, or the to identify type, properties, or sequence of the device in a manufacturing batch.

Stage 5:

Lastly, a quality control element of the automation may be applied. This element may include checking bounds of mass, the bounds of size, the curvature of the body, continuity of bodies within the device, finite element analysis for strength, and bounds of clearance values to ensure the device meets all specifications needed for manufacturing. After the quality control, the CAD file may be converted to a new file type for manufacturing. File types may include but are not limited to: STL, OBJ, VRML, and X3G. The file may or may not be sent to a new database or used on the current device. The file can then be converted into a physical model of the device using either additive or subtractive manufacturing techniques.

With the currently described autonomous vertical integration herein, one of the most important improvements is time to produce the device. According to the present invention, the consumer may receive the necessary device on a significantly shortened time frame. Due to the current invention, devices can now be produced and purchased at a lower cost. This allows for a larger market to interact with the object—improving the quality of life of a larger populus.

The device can be created better with the described algorithm than any individual or group of individuals. Being able to mathematically decide the form based on tangibles creates a superior device and eliminates the possibility of any human error during device creation. Superiority comes in the form of improved fitment, increased comfort, greater ultimate strength, and a larger resistance to shearing forces.

Lastly, the automation allows for a consistent device. Despite being custom, a wearer will be able to accurately predict the interaction the device has with his or her body. Another benefit of the consistency is the removal of human error. The device will be seamless and ensure the wearer does not wait longer to address the needs that would be fulfilled by the product.

In application, by way of an example, a patient with multicompartment knee OA, including patellofemoral and medial compartment OA, would visit a doctor after experiencing knee pain during activity. The patient may also consult a doctor remotely using telehealth. The doctor would identify indications of knee OA, including reduced stability, user pain during specific activities such as climbing stairs, and potential joint deformity. At this stage, a custom brace may be prescribed. The doctor, another health professional, or the user may scan the joint using software on a phone or tablet. The scan data would then be uploaded to a cloud-based server. Data may be cleaned, processed, or converted into a different file type on the device used to take the scan or after being transferred to the server. The prescriber may also provide supporting radiographic data, such as an MIll, through the health network's user interface, which may then be sent to the same or a different cloud-based server. Data from the same server or different servers within the network may be paired by a unique identifier, such as a patient or job ID number. Quality analysis of the data may be performed either on the device or user interface where the data is collected or in the server on which the data is stored. The user or doctor may receive error messages indicating that data needs to be recaptured if it does not pass quality standards.

Processed data will then be transferred to a computer system on which the software comprising the code for operations from Stages 2 through 5 are performed (as described above). An operator may oversee the process as performed by the software. The software may present them with reports, in real time or at different stages of the process to assess the accuracy and progress of the device modeling. The operator may approve performance of different functions between or within different stages of the process for the software to proceed in modeling. Alternatively, they may opt for corrective action, manually or through activation of a different code/software function, if the quality of device modeling is deemed insufficient based on reports or observation. Once the device has been fully formed, quality control analysis in stage 5 may be implemented on the same computer system or a separate system to achieve a final, approved device for fabrication. The modeling system may be integrated with the fabrication system, which controls 3D printing output, through an API to automatically queue and print the digitally represented device. The final device may be fabricated as one continuous part from one or more materials. Alternatively, additional components may be added during an assembly process to yield a final device. The entire process, from data collection to delivery of a final, custom fit device to fulfill the user need may be completed, in aspects, within 12 hours based on the current, automated system as described. A fully automated system that performs the above process is exemplified in FIG. 6.

Embodiments of the invention also include a computer readable medium comprising one or more computer files comprising a set of computer-executable instructions for performing one or more of the calculations, stages, processes and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Figure 6:
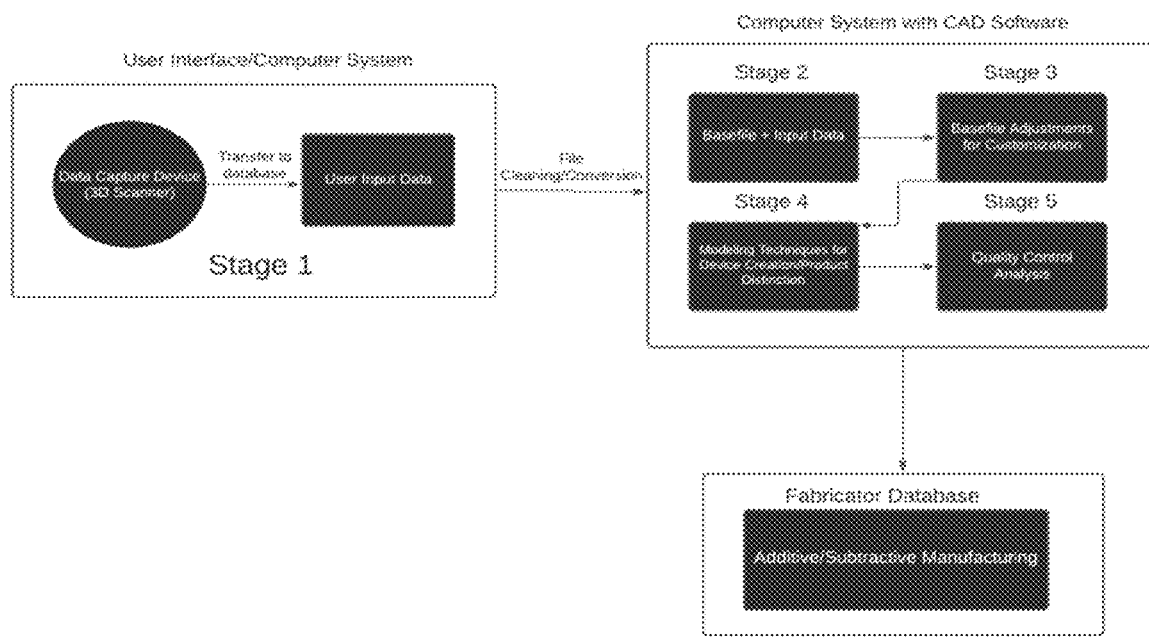
FIG. 6 depicts an exemplary form of a fully or partially automated system that operates the fully or partially automated process depicted in FIG. 1 according to an embodiment of the current invention.

Embodiments of this disclosure include one or more computers or devices loaded with a set of the computer-executable instructions described herein (FIG. 6). The computers or devices may be a general purpose computer, a special-purpose computer, or other programmable data processing apparatus to produce a particular machine, such that the one or more computers or devices are instructed and configured to carry out the calculations, processes, stages, operations, algorithms, statistical methods, formulas, or computational routines of this disclosure. The computer or device performing the specified calculations, processes, stages, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, stages, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection. In embodiments, the GUI provides reporting functions regarding the status of the code and related medical device construction. Reports may include real-time demonstration of the device construction, status of a brace in a pipeline from data collection through design through fabrication completion. The reports may provide quality control data to show that the device has sufficient strength, fit, and meets the specifications outlined by the data inputs relative to the aspects described in Stage 5. The reports may provide a user the ability to approve an output at any stage of the process to proceed to the following stage, present more data, or perform corrective actions, either manually or automatically by activating a secondary code.

All or part of the product may incorporate aspects of artificial intelligence or machine learning to continually improve the quality of outputs at each stage of the process. In aspects, the machine learning component may optimize the speed and reduce the required computing power of the program by performing any function of Stages 2-5 and optimizing the process (e.g. translations and rotations) to achieve a more direct end result. For example, the algorithm may limit the degrees of motion or minimize the number of translations of a strap slot or other component that is being automatically placed on the device base frame. It may optimize to apply select modifications (e.g. translation and rotation) to groups of components or features in parallel. The machine learning program may optimize to improve device fitment based on data collected following device use by the customer, which may be submitted via a survey or feedback form. Data may be collected via sensors in the device which are uploaded continuously via wifi or bluetooth to a database, or are uploaded at intervals in batches manually or automatically (e.g. an export from the device memory). For example, pressure sensor readings within the brace frame may lead to an automated adjustment of the curvature of the device at a given location based on the average anticipated interaction with the user's anatomy. The machine learning algorithm may analyze this data in combination with initial input data defined in Stage 1 to further optimize design of one subset of devices or all devices within the software's library.

The invention includes devices fabricated using the disclosed method, software system, product, or computer system detailed above.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A computer-implemented method for automating a design and manufacture of a custom designed joint brace or orthotic device, the method comprising:
   providing a digital depth camera capable of three-dimensional (3D) scanning;
   obtaining a 3D surface scan of a human joint, limb, or body part using the depth camera;
   processing compiled scan data;
   converting geometric relationships based on points derived from the 3D surface scan to instructions or values;
   applying digital transformations to cross-sections and/or device reference points to modify a virtual 3D pre-designed base device based on the instructions or values to create a virtual custom device; and
   manufacturing the joint brace or orthotic device based on the virtual custom device.

2. The method according to claim 1, further comprising:
   separating the virtual 3D pre-designed base device into two or more component parts;
   representing a shape of the two or more component parts with a pre-defined number of cross-sections;
   using three or more points derived from the 3D surface scan or reference geometries to define the pre-defined number of cross-sections;
   calculating geometric relationships of the points derived from the 3D surface scan or the reference geometries with the 3D surface scan;
   calculating one or more translations for three or more device reference points or device reference geometries within each cross-section for fitting to the 3D surface scan;
   applying the translations to the device reference points or the device reference geometries;
   calculating rotations for each of the three or more device reference points or device reference geometries for fitting to the 3D surface scan;
   applying the calculated rotations to all the device reference points or device reference geometries.

3. The method according to claim 2, further comprising averagely distributing a distance between the pre-defined number of cross-sections of the virtual 3D pre-designed base device to span the entire joint brace or orthotic device.

4. The method according to claim 1, further comprising:
   digitally separating the virtual 3D pre-designed base device into two or more component parts;
   aligning and fixing distances and relative orientations between the two or more component parts.

5. The method according to claim 1, further comprising:
   using three or more points derived from the 3D surface scan or reference geometries to define a pre-defined number of cross-sections of the virtual 3D pre-designed base device;
   determining two or more points derived from the 3D surface scan of the three or more points derived from the 3D surface scan or reference geometries as control points and connecting them with b-spline interpolation to define a boundary of one or more of the cross-sections.

6. The method according to claim 1, further comprising using three or more points derived from the 3D surface scan or reference geometries to define individual cross-sections of the virtual 3D pre-designed base device, and determining at least one device reference point of the device reference points or reference geometries as a center of one or more of the individual cross-sections.

7. The method according to claim 1, further comprising:
   calculating a geometric relationship of two or more points derived from the 3D surface scan;
   identifying a first device reference point on the virtual 3D pre-designed base device and a closest point derived from the 3D surface scan;
   applying translations to the first device reference point on the virtual 3D pre-designed base device based on its distance from the closest point derived from the 3D surface scan and the geometric relationship of the two or more points derived from the 3D surface scan.

8. The method according to claim 1, further comprising:
   determining a first point derived from the 3D surface scan;
   determining a device reference point on the 3D pre-designed base device that is nearest to the first point derived from the 3D surface scan;
   using the first point derived from the 3D surface scan and the device reference point, calculating a translation for the device reference point on the 3D pre-designed base device for fitting the virtual 3D pre-designed base device to the 3D surface scan; and
   generating a 3D translation vector based on the calculated translation of the device reference point to create a contact point between one or more pre-defined cross sections of the virtual custom device and the 3D surface scan.

9. The method according to claim 1, further comprising:
   determining one or more device reference points on the virtual 3D pre-designed base device or virtual 3D custom device;
   calculating rotations for one or more of the one or more device reference points to fit the virtual 3D pre-designed base device or virtual 3D custom device to the 3D surface scan;

calculating a rotation angle that minimizes a distance between a non-contact point of the one or more device reference points on the virtual 3D pre-designed base device or virtual 3D custom device and the 3D surface scan.

10. The method according to claim 1, further comprising digitally writing the virtual custom device into permanent storage using a computer-aided design format.

11. The method according to claim 1, further comprising:
adding auxiliary components to the joint brace or orthotic device, comprising one or more of strap slots, tensioning components, serial numbers, company logo, company name, or other custom designs; and
running a quality control to ensure that the body design of the joint brace or orthotic device complies with industry standards.

12. The method according to claim 1, further comprising loading patient medical information into a database and using the patient medical information to aid in designing the joint brace or orthotic device.

13. The method according to claim 1, further comprising loading patient medical information into a database, wherein the patient medical information includes one or more of Q angle of a user's joint, body mass index, age, weight, height, degree of patient pain, location of pain, location of pain during movement, radiographic data, or intended activity, wherein the patient medical information is incorporated automatically or semiautomatically into a mechanical design of the joint brace or orthotic device.

14. The method according to claim 1, wherein radiographic data, Magnetic Resonance Imaging (MRI) data, Computed Tomography (CT) scan data, Position Emission Tomography (PET) scan data, X-ray data, fluoroscopy data, or ultrasound data, is input into a database and incorporated automatically or semiautomatically into a mechanical design of the joint brace or orthotic device.

15. The method according to claim 1, further comprising automatically performing a quality control analysis on the 3D surface scan, the joint brace or orthotic device, or the virtual custom device.

16. The method according to claim 1, wherein mechanical impedance or tissue elasticity of a body part are calculated based on patient medical information, and wherein the mechanical impedance or tissue elasticity of the body part are used to improve the fit and function of the joint brace or orthotic device.

17. The method according to claim 1, wherein machine learning algorithms are applied to continually improve the quality of outputs, optimize a speed of designing or manufacturing, reduce required computing power, optimize transformations to achieve a more direct end result, or combinations thereof.

18. The method according to claim 1, further comprising:
identifying locations of high stress concentrations in the virtual custom device;
applying fillets to the identified locations to improve the strength and/or durability of the virtual custom device.

19. The method according to claim 1, wherein a type and number of component subsystems of the joint brace or orthotic device are added to the custom virtual device depending on the 3D pre-designed base device that is selected.

20. The method according to claim 1, further comprising:
performing automated mechanical analysis of the virtual custom device; and
increasing or decreasing the infill geometry or infill density of the virtual custom device at cross sections to improve the virtual custom device's anticipated strength to weight ratio, or to improve the strength and/or durability of the joint brace or orthotic device.

21. A system for designing a custom-fitting joint brace or orthotic device comprising the following:
at least one processor;
at least one memory device coupled to the processor capable of storing computer-readable instructions which, when executed by the at least one processor, cause the system to perform the following:
using a depth camera to obtain a three-dimensional (3D) surface scan of a human limb joint, or body part using 3D scanning;
processing compiled scan data;
converting geometric relationships based on points derived from the 3D surface scan to instructions or values;
applying digital transformations to cross-sections and/or device reference points to modify a virtual 3D pre-designed base device based on the instructions or values to create a virtual custom device; and
manufacturing the joint brace or orthotic device based on the virtual custom device.

22. The system according to claim 21, further comprising:
uploading the compiled scan data to a database;
processing and converting the compiled scan data into a format that is capable of being represented as a 3D digital object in a computer aided design system component;
defining geometric constraints based on the compiled scan data and/or 3D digital object;
digitally fitting a virtual 3D pre-designed base device to the 3D digital object;
adapting the virtual 3D pre-designed base device to a virtual custom device based on the obtained 3D surface scan and the defined geometric constraints;
performing quality control analysis on the virtual custom device;
sending a virtual custom device file to a database for fabrication.

23. A non-transitory computer-readable medium having stored instructions that, when executed by one or more processors, cause a computing device to perform functions comprising:
obtaining a 3-dimensional (3D) surface scan of a human joint, limb, or body part using 3D scanning with a depth camera;
processing compiled scan data;
converting geometric relationships based on points derived from the 3D surface scan to instructions or values; and
applying digital transformations to cross-sections and/or device reference points to modify a virtual 3D pre-designed base device based on the instructions or values to create a virtual custom device.

* * * * *